Figure 1:
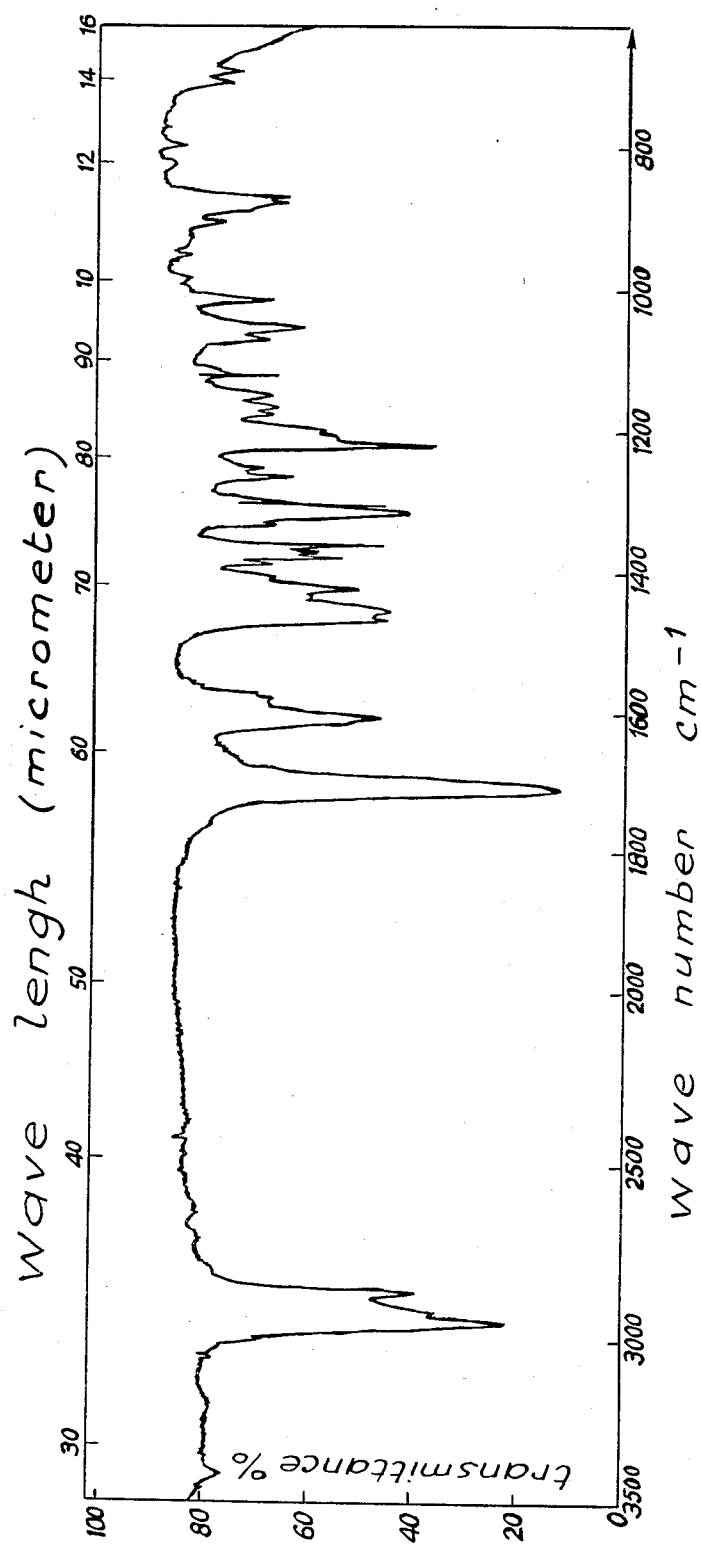

United States Patent [19]

Joulain

[11] Patent Number: 4,541,948
[45] Date of Patent: Sep. 17, 1985

[54] PERFUMES CONTAINING POLYALKYL SUBSTITUTED INDAN-1-ONES AND PROCESS FOR PREPARING THE COMPOUNDS

[75] Inventor: Daniel R. Joulain, Grasse, France

[73] Assignee: P. Robertet & Cie [Societe Anomyme], Grasse, France

[21] Appl. No.: 470,327

[22] Filed: Feb. 28, 1983

[30] Foreign Application Priority Data

Mar. 11, 1982 [FR] France .................. 82 04293

[51] Int. Cl.$^4$ .................. A61K 7/46; C07C 49/36
[52] U.S. Cl. .................. 252/522 R; 568/326
[58] Field of Search .................. 252/522 R; 568/326

[56] References Cited

U.S. PATENT DOCUMENTS

| 2,815,381 | 12/1957 | Carpenter et al. | 252/522 R |
| 2,815,382 | 12/1957 | Carpenter et al. | 252/522 R |
| 3,408,399 | 10/1968 | Galantay | 568/326 |
| 3,769,348 | 10/1973 | Wood et al. | 568/326 |

FOREIGN PATENT DOCUMENTS 09302 9/1983 European Pat. Off.

OTHER PUBLICATIONS

Marquardt, "Helvetica Chimica Acta", vol. 48, No. 159, (1965), pp. 1476-1485.

*Primary Examiner*—Anton H. Sutto
*Attorney, Agent, or Firm*—Bucknam and Archer

[57] ABSTRACT

The invention relates to new polyalkyl indan-1-ones, to processes for manufacturing them and to the use thereof in perfumes. The new products are polyalkyl substituted hydrindacen-1-ones and polyalkyl substituted hexahydro benz(f) inden(1H)-1-ones belonging to the family of substances defined by the following formula:

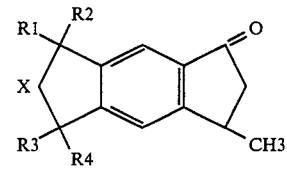

in which R1, R2, R3, R4 are H or an alkyl radical having one to three atoms of carbon and X is a —CHR5— group or a —CHR5—CHR6— group in which R5 and R6 are H or CH3 and at least three of the radicals R1, R2, R3, R4, R5 and R6 are alkyl radicals.

14 Claims, 3 Drawing Figures

PERFUMES CONTAINING POLYALKYL SUBSTITUTED INDAN-1-ONES AND PROCESS FOR PREPARING THE COMPOUNDS

The present invention relates to new products constituted by polyalkyl substituted derivatives of indan-1-ones, to processes for preparing these products and to applications of these products in perfume compositions.

Products with musk-like odors are much sought after in perfumery for various uses such as the preparation of extracts, toilet waters, cosmetic or body hygiene products, household cleaning products, etc.

Natural musk extracted from the musk-deer is very expensive and chemists have sought to develop synthetic products emitting an odor which is as close as possible to that of natural musk. A very large number of products with musk-like odor have been synthesized, but only a few are exploited on an industrial scale.

Among them, a certain number possess a ketonic function borne by a polycyclic system comprising an aromatic ring. The following derivatives of indanes are known in particular and used for their musk-like odor:
7-acetyl 3,3-dimethyl 5-tertiobutyl indane
6-acetyl 1,1,2,3,3,5-hexamethyl indane
6-acetyl 1-isopropyl 2,3,3,5-tetramethyl indane.
These derivatives are known respectively under the names of Celestolide, Phantolide and Traseolide. The latter is described in French Pat. No. 78 05455 (2 460 913) to NAARDEN.

A derivative of tetraline is also known, viz.:
7-acetyl 1,1,3,4,4,6-hexamethyl 1,2,3,4-tetrahydro naphthalene,
known under the name of Tonalide.

All these known products comprise a ketone function forming part of an acetyl substituent and are indanes or a tetraline comprising a six-membered ring joined to a five-membered or six-membered ring.

Attempts have been made to synthesize polycyclic hydrocarbons in which the ketone function is part of a ring.

The publication J. Agr. Food Chem. 1967, 15, 6 mentions two substituted derivatives of indacenes, viz. 5,5,7,7-tetramethyl 3,5,7,7-tetrahydro indacen(2H)1-one and 5,5,8,8-tetramethyl 2,3,5,6,7,8-hexahydro benz(f) inden-1-one.

These two derivatives of indacenes give off a weak musk-like odor.

It is an object of the invention to procure new, synthetic, polyalkyl substituted, derivative products of indanones having a strong musk-like odor very similar to that of natural musk.

Applicant has discovered that this result is achieved by means of new polyalkyl derivatives of indan-1-ones which comprise a polycyclic system composed of a first benzene ring to which is joined a second five-membered ring bearing a ketone function in 1 position, no substitute in 2 position and one methyl radical in 3 position and comprising a third ring joined to the benzene ring which is either a five-membered ring symmetrical with respect to the second ring (in which case the products are derivatives of hydro(s)indacen(2H)-1-one), or a six-membered ring (in which case the products are derivatives of hydrobenz(f) inden(1H)-1-one).

In both cases, the third ring comprises at least three alkyl substituents selected from methyl, ethyl or propyl, normal or iso.

In the course of the numerous trials which have been carried out, Applicant has determined that the group constituted by a ketone function in 1 position, no substituents in 2 position and one methyl radical in 3 position, was necessary in order to obtain products which give off a strong musk-like odor very similar to the typical odor of natural musk.

Applicant has determined that the presence of a methyl substituent in 2 position, with or without a methyl substituent in 3 position, led to a synthetic product without usable odor. Similarly, he determined that the presence of two methyl substituents in 3 position led to a synthetic product without usable odor.

Finally, Applicant has established that the presence of alkyl substituents on the third ring was important for the fragrant quality of the product and that only derivatives comprising at least three methyl, ethyl or propyl substituents fixed to the third ring were of any interest in the perfume industry.

Taking the foregoing results into account, the invention relates, by way of new products, to polyalkyl substituted derivatives of indan-1-ones belonging to the family of synthetic substances defined by general formula:

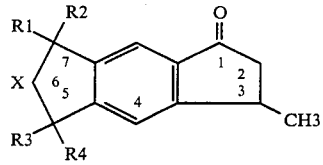

in which R1, R2, R3, R4 denote, separately, a hydrogen or an alkyl radical having one to three atoms of carbon, in which X represents a —CHR5— group or a —CHR6—CHR6— group, in which R5 and R6 represent, separately, a hydrogen or a methyl radical and in which at least three of the radicals R1, R2, R3, R4, R5 and R6 are alkyl radicals, which derivatives all comprise a ketone function in 1 position, no substituent in 2 position, one methyl group in 3 position and a five-membered or six-membered ring, symmetrical with respect to the ring bearing the ketone function, comprising at least three alkyl substituents.

More particularly, the invention relates to a first family of new chemical products which are polyalkyl derivatives of hydro(s) indacen(2H)-1-one defined by general formula:

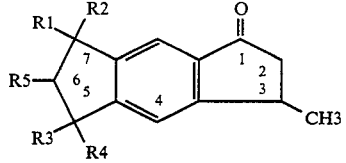

in which R1, R2, R3, R4 represent a hydrogen or an alkyl radical having one to three carbon atoms, R5 represents a hydrogen or a methyl radical and at least three of the radicals R1, R2, R3, R4, R5 are alkyl radicals.

The invention also relates to a second family of new chemical products which are polyalkyl derivatives of hydro benz(f) inden(1H)-1-one, defined by general formula:

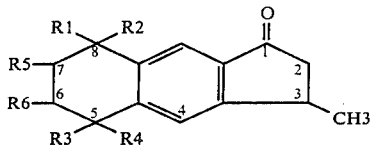

in which R1, R2, R3, R4 represent a hydrogen or an alkyl radical having one to three carbon atoms, R5, R6 represent a hydrogen or a methyl radical and at least three of the radicals R1, R2, R3, R4, R5, R6 are alkyl radicals.

The invention also relates to new processes for preparing the substituted derivatives according to the invention.

Various processes for synthesizing substituted derivatives of indan-1-ones are known which might be used for preparing the derivatives according to the invention. These known processes necessitate several steps and are not economical.

A process for preparing various indan-1-ones is known, whereby an aromatic derivative is directly reacted with an α, β-ethylene acid in the presence of polyphosphoric acid (cf. Article by F. H. Marquart in Helv. Chem. Acta 1965, 48, 1476).

This known cyclization process has already been used in the case of derivatives comprising an aromatic cycle sufficiently reactive with respect to reactions of aromatic electrophile substitution. In all known applications, the substances used always comprise an aromatic cycle activated by the presence of alkoxyl substitutes, these latter acting by mesomeric electrodonor effect.

Now, the preparation of derivatives according to the invention necessitates starting from an aromatic derivative comprising an aromatic cycle substituted by alkyl radicals and, in this case, the electrodonor activating effect of the substitutes on the aromatic cycle is of the inductive type, whose force is much attenuated with respect to that of the mesomeric effect of the alkoxyl substitutes.

Applicant has discovered that, under appropriate operational conditions, it was possible to compensate, in determining manner, the low reactivity of the aromatic compounds comprising alkyl substituents and to extend thereto the domain of application of the known process of cyclization consisting of reacting thereon an α,β-ethylene acid in the presence of polyphosphoric acid.

Moreover, Applicant has made an improvement to the known process. He has, in fact, discovered that, to effect condensation, it was advantageous to use, not α,β-ethylene acids, but methyl or ethyl esters of these acids in order to facilitate purification of the product resulting from the reaction.

The processes according to the invention consist of subjecting a known aromatic derivative selected from the group of polyalkyl, indanic or tetralinic hydrocarbons, to a reaction of cycli-alkylacylation by an α,β-ethylene acid or, preferably, by a methyl or ethyl ester of an α,β-ethylene acid in the presence of polyphosphoric acid. The reaction takes place in a reactor at a temperature of between 90° C. and 150° C. and, preferably, between 120° C. and 125° C. if an ester of ethylene acid is used and between 130° C. and 135° C. if an ethylene acid is used.

It will be recalled that the known polyalkyl indanic hydrocarbons or polyalkyl-indanes are defined by general formula:

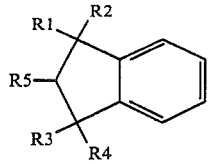

in which R1, R2, R3, R4, R5 are H or alkyl radicals.

For preparing the substituted derivatives according to the invention, polyalkyl-indanes are used in which R5=H or CH3 and R1, R2, R3, R4 represent, separately, H or an alkyl radical having one to three atoms of carbon.

The majority of the polyalkyl indanic derivatives are known and it is known how to prepare them industrially.

For example, the 1,1,2,3,3-pentamethyl indane and the 1,1,3,3-tetramethyl indane which are used in the examples described hereinbelow, may be prepared according to a process described by D. B. Spoelstra et Col., in the publication Rec. Trav. Chim. Netherlands, 1963, 82, 1100.

The polyalkyl tetralinic hydrocarbons or polyalkyl tetrahydronaphthalenes are defined by formula:

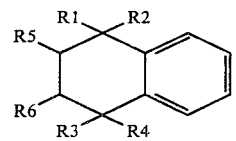

in which R1, R2, R3, R4, R5, R6 are, separately, H or an alkyl radical.

For carrying out the process according to the invention, the derivatives in which R5 and R6 represent, separately, H or CH3 and R1, R2, R3, R4 represent H or a methyl, ethyl, propyl or isopropyl radical, are used.

It is known how to prepare these aromatic derivatives. For example, the 1,1,4,4-tetramethyl 1,2,3,4-tetrahydro naphthalene which is used in the following examples, may be prepared by the method described by G. Baddeley and M. Gordon in J. Chem. Soc. 1958, 4379.

EXAMPLE 1

Preparation of 3,5,5,6,7,7 hexamethyl 3,5,6,7-tetrahydro(s) indacen(2H)-1-one

Into a six-liter reactor are poured 4500 g of polyphosphoric acid ($d^{25}=2.0$ minimum), which are heated with mechanical stirring up to the temperature of 132° C.±3° C. A solution preheated to 50° C. of 240 g of crotonic acid and of 470 g of 1,1,2,3,3-pentamethyl indane is progressively poured in 20 to 30 minutes. For the whole duration of addition and during the 45 minutes following, the same conditions of temperature and stirring are maintained. At the end of this period, the reactional mass is rapidly cooled to about 70° C. and it is poured over crushed ice and energetically stirred. After decantation of the organic phase and extraction of the aqueous phase with toluene (2×1000 ml), the organic phases are combined and washed to neutrality by means of a 10% aqueous solution of sodium carbonate, then water.

After elimination of the toluene under reduced pressure, 572 g of crude product are obtained which are subjected to a first purification in a bulb type distiller. 454 g of distillate having a boiling point lower than 200° C. under a pressure of 0.1 mmHg are collected. A second purification of this distillate is made in a distillation apparatus equipped with a 50 cm long Vigreux column. In this way, 240 g of 1,1,2,3,3 pentamethyl indane which has a boiling point of 80°–85° C. under 2 mmHg are, on the one hand, obtained. This constitutes the residue of what was introduced into the reactor but which did not react. It may be re-used in a further reaction.

On the other hand, 180 g are obtained of a product having a boiling point of 140°–142° C. under 0.1 mmHg and a refraction index $n_{20}^D = 1.551$ and which has been identified as being:

3,5,5,6,7,7-hexamethyl 3,5,6,7-tetrahydro(s) indacen(2H)-1-one.

The weight of 1,1,2,3,3 pentamethyl indane converted is therefore 230 g and the molecular yield with respect to the quantity of pentamethyl indane converted is 57%.

Figure 2:
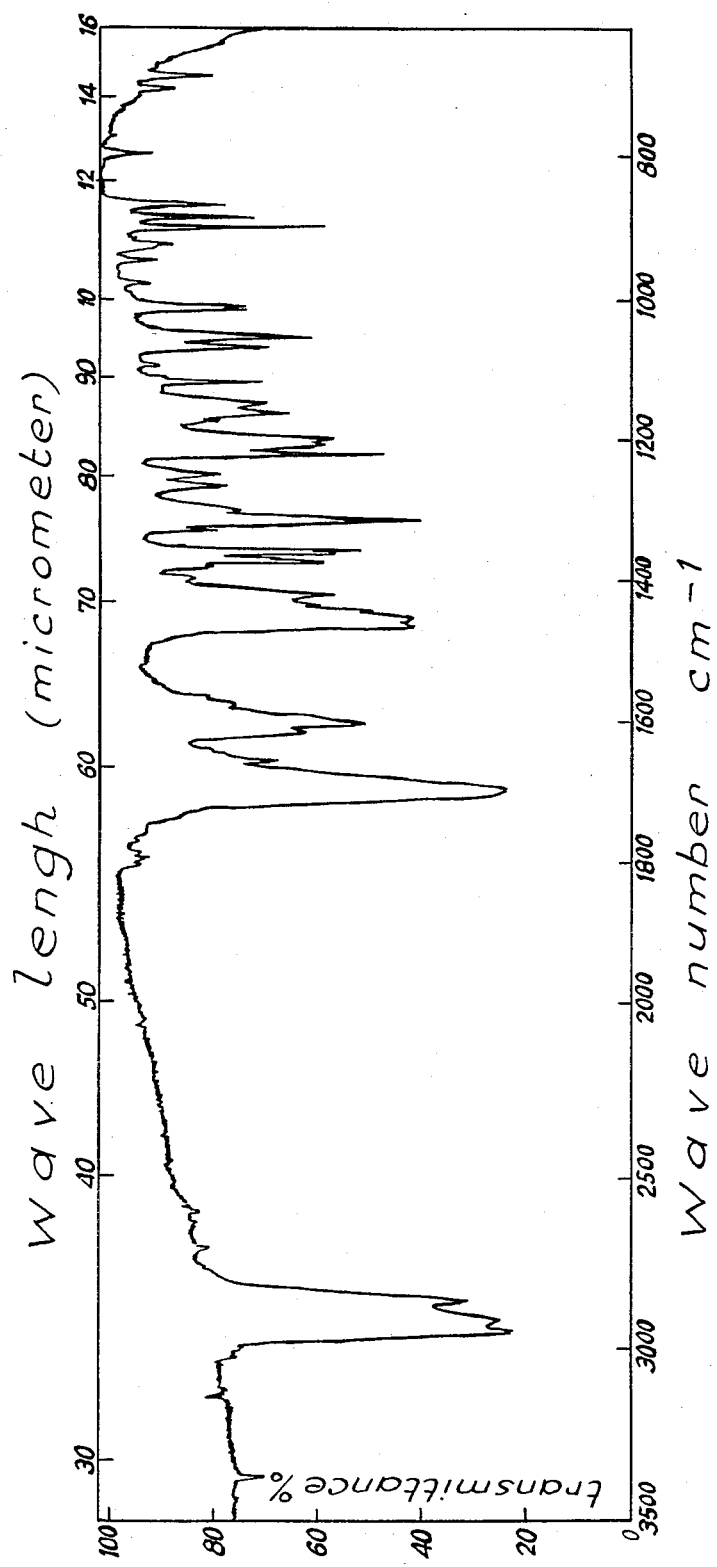
Figure 3:
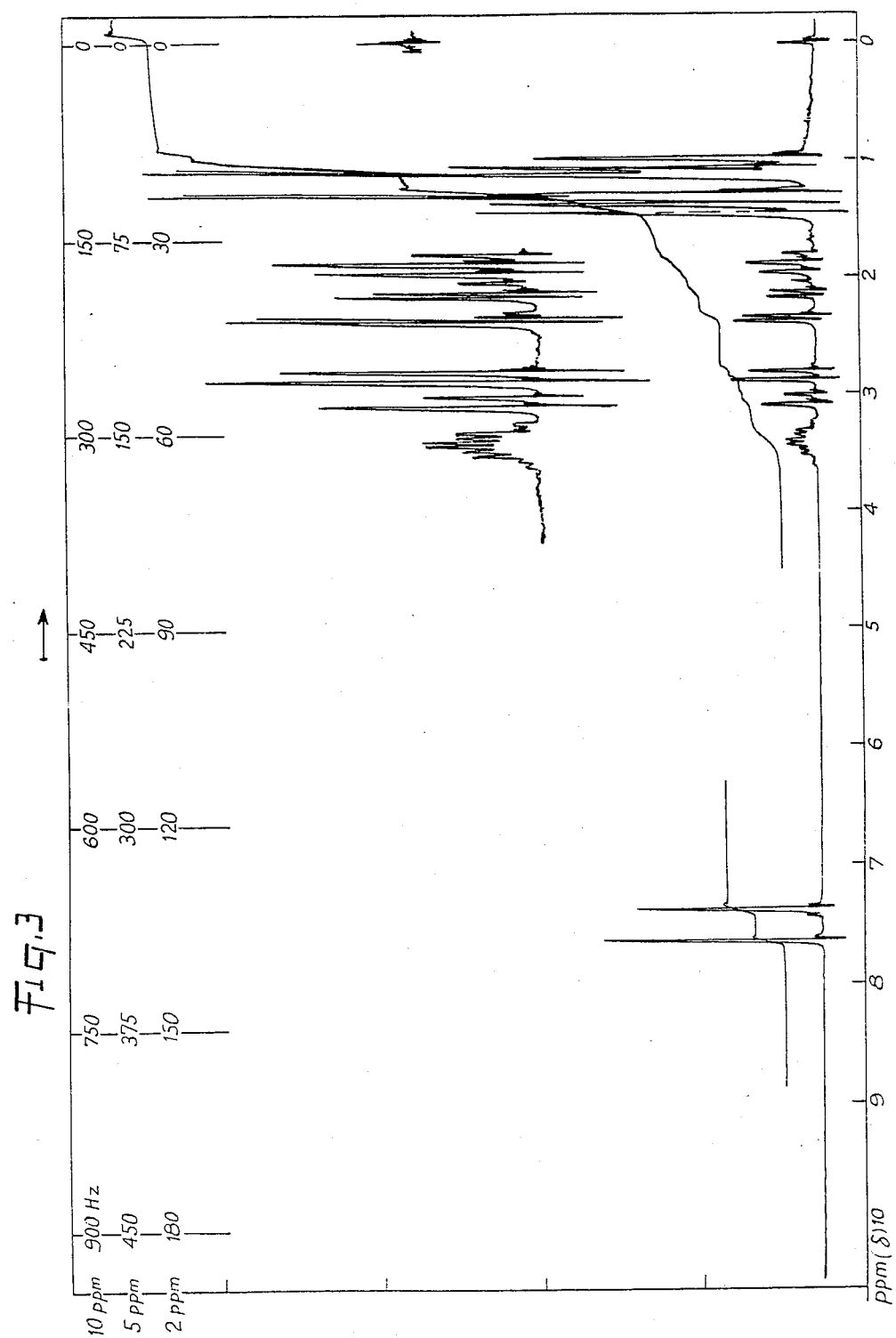

FIG. 1 shows the infrared absorption spectrum of the product obtained which has been identified as being a mixture of two isomers which differ from each other by the relative position in space of two methyl radicals in 3 and 6 position. The mixture of the two isomers may be used as such in perfumes and perfume compositions. By recrystallization from ethyl alcohol, a pure isomer having a melting point of 110° C. has been isolated. FIGS. 2 and 3 respectively show the infrared absorption spectrum and the nuclear magnetic resonance (NMR) spectrum at 90 MHz of this pure isomer.

The reaction scheme obtained in this Example is as follows:

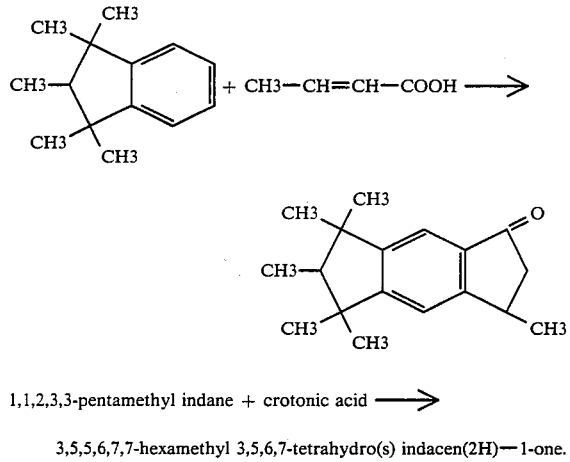

1,1,2,3,3-pentamethyl indane + crotonic acid ⟶

3,5,5,6,7,7-hexamethyl 3,5,6,7-tetrahydro(s) indacen(2H)—1-one.

EXAMPLE 2

In this Example, the starting aromatic derivative and the final product obtained are the same as those of Example 1. The crotonic acid is replaced by an ester, viz. methyl or ethyl crotonate. 120 g of methyl crotonate are progressively added in two hours to a mixture of 1140 g of polyphosphoric acid and 113 g of 1,1,2,3,3-pentamethyl indane, stirred and maintained constantly at 125° C.±3° C. The mixture is stirred at this temperature for three hours, then cooled to 70° C. and the same treatments are carried out as in Example 1.

Finally, 14 g of 1,1,2,3,3-pentamethyl indane which did not react and which can be recycled and 97 g of 3,5,5,6,7,7-hexamethyl 3,5,6,7-tetrahydro(s) indacen(2H)-1-one, are separated.

The molecular yield is 71.9% with respect to the pentamethyl indane converted.

By replacing the methyl crotonate by an equivalent quantity of ethyl crotonate, a similar result is obtained.

The product obtained in these two Examples releases a very powerful musk-like odor, very similar to the odor of natural musk.

EXAMPLE 3

Preparation of 3,5,5,7,7-pentamethyl 3,5,6,7-tetrahydro(s) indacen(2H)-1-one.

The operational conditions are the same as in Example 1. 4500 g of polyphosphoric acid, 290 g of crotonic acid and 450 g of 1,1,3,3-tetramethyl indane are used. 98 g of unchanged 1,1,3,3-tetramethyl indane which may be recycled, and 300 g of a product having a boiling point of 136°–138° C. under 0.1 mmHg and a melting point of 83°–84° C. are recovered. The infrared absorption spectrum presents a characteristic, very high main band at 1710 waves cm$^{-1}$. The molecular yield is 61.3% with respect to the converted 1,1,3,3-tetramethyl indane.

The NMR spectrum (200 MHz, CDCl3) presents four singlets at 1.32, 1.33, 1.34 and 1.35 ppm (four geminate methyl groups); a doublet at 1.42 ppm (J=7.4 Hz; methyl in 3 position); a singlet at 1.98 ppm (CH2 group in 6); two doublets of doublets centred at 2.29 ppm (J=3.6 and 19 Hz) and at 2.96 ppm (J=7.6 and 19 Hz) attributed to the group CH2 in 2; a complex multiplet centred at 3.41 ppm (J=3.6; 7.6 and 7.4 Hz, tertiary proton in 3) and two singlets at 7.25 and 7.54 ppm (two isolated aromatic protons). The product obtained has been identified as being 3,5,5,7,7-pentamethyl 3,5,6,7-tetrahydro(s) indacen(2H)-1-one. This product releases a powerful musk-like odor, slightly weaker and milder than that of the product obtained in Examples 1 and 2 and very similar to that of the synthetic macrocyclic oxa-musks.

EXAMPLE 4

Preparation of 2,3,5,5,6,7,7-heptamethyl 3,5,6,7-tetrahydro(s) indacen(2H)-1-one The operational conditions are the same as in Example 1. The following reagents are used: 3800 g of polyphosphoric acid, 260 g of tiglic acid and 377 g of 1,1,2,3,3-pentamethyl indane. At the end of reaction and purification, 128 g of unchanged 1,1,2,3,3-pentamethyl indane which can be recycled and 278.5 g of a product having a boiling point at 136°–156° C. under 0.1 mmHg, are obtained. The infrared absorption spectrum presents two characteristic main bands at 1705 cm$^{-1}$ (very high) and 1612 cm$^{-1}$ (high). The product obtained is a mixture of isomers which have been identified as being 2,3,5,5,6,7,7-heptamethyl 3,5,6,7-tetrahydro(s) indacen(2H)-1-one.

This product has no musk-like odor. This test shows that the musk-like odor is linked not only with the presence of a methyl radical in β position but also with the absence of substitute in α position.

EXAMPLE 5

Preparation of 3,5,5,8,8-pentamethyl 2,3,5,6,7,8-hexahydro benz(f) inden(1H)-1-one The operational conditions are the same as in Example 1. The following reagents are used: 2400 g of polyphosphoric acid, 145 g of crotonic acid and 240 g of 1,1,4,4,-tetramethyl tetraline.

After reaction and separation, 51 g of unchanged 1,1,4,4-tetramethyl tetraline which can be recycled, and 192 g of a product having a boiling point of 143°–144° C. under 0.1 mmHg and a melting point at 80° C. (ethanol), are obtained.

The molecular yield is 74.5% with respect to the 1,1,4,4-tetramethyl tetraline converted.

The infrared spectrum presents two characteristic bands, one at 1710 cm$^{-1}$ (very high) and the other at 1612 cm$^{-1}$ (high).

The NMR spectrum (200 MHz, CDCL3) presents two singlets at 1.30 and 1.32 and two singlets together at 1.34 ppm (four geminate methyl groups); a doublet at 1.40 ppm (J=7 Hz, methyl in 3); a singlet at 1.72 ppm (two CH2 groups in 6 and 7); two doublets of doublets centred at 2.26 ppm (J=3.6 and 19 Hz) and 2.92 ppm (J=7.6 and 19 Hz) attributed to a CH2 group in 2; a complex multiplet centred at 3.40 pm (J=3.6; 7.6 and 19 Hz) attributed to a tertiary proton in 3 and two singlets at 7.48 and 7.76 ppm (two isolated aromatic protons).

The product thus obtained has been identified as being 3,5,5,8,8-pentamethyl 2,3,5,6,7,8-hexahydro benz(f) inden(1H)-1-one.

This product releases a musk-like odor, which is weaker than that of the products obtained in Examples 1 to 3 and which is similar to that of other aromatic polycyclic musks.

The reaction scheme produced in Example 5 is as follows:

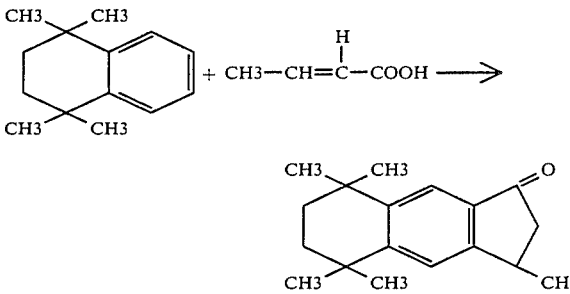

1,1,4,4-tetramethyl tetraline + crotonic acid ⟶

3,5,5,6,8,8-pentamethyl 2,3,5,6,8-hexhydro benz(f) inden(1H)—1-one

EXAMPLE 6

Preparation of 2,3,5,5,8,8-hexamethyl 2,3,5,6,7,8-hexahydro benz(f) inden(1H)-1-one The operational conditions are the same as in the preceding Example and the crotonic acid is replaced by tiglic acid.

4300 g of polyphosphoric acid, 300 g of tiglic acid and 430 g of 1,1,4,4-tetramethyl tetraline are reacted.

After separation of the reaction products, 113 g of 1,1,4,4-tetramethyl tetraline which has not reacted and which may be re-used, and 328 g of a product which has a melting point at 80°–83° C. (ethanol) and a boiling point at 142°–144° C. under 0.1 mmHg, are obtained. The infrared spectrum of the product shows two characteristic main bands, one at 1705 waves cm$^{-1}$ which is very high and the other at 1612 waves cm$^{-1}$ which is high.

The product obtained is identified as a mixture of two isomers of 2,3,5,5,8,8-hexamethyl 2,3,5,6,7,8-hexahydro benz(f) inden(1H)-1-one.

The molecular yield of the reaction is 76% with respect to the 1,1,4,4-tetramethyl tetraline converted.

The product obtained in this Example has no musklike odor, which confirms the negative result described in Example 4.

The aromatic derivatives which were subjected in the Examples described to a reaction of cycli-alkylacylation, are polymethyl indanes or polymethyl tetralines. It is specified that equivalent results have been obtained from polyethyl or polypropyl indanes or tetralines and products have also been obtained which release a more or less pronounced musk-like odor.

The duration of the reaction may be greater than the total duration of the order of 75 minutes which corresponds to the Examples described. However, when α,β-ethylene acids are used, a longer duration of reaction brings about the formation of polymerization products and tests carried out have shown that a total duration of reaction of between 45 and 70 minutes is preferred.

Tests have also been carried out to obtain products not comprising any methyl radical in β position but comprising a methyl radical in α position.

These tests have led to products releasing no usable musk-like odor.

Finally, tests carried out show that the musk-like odor is linked with the presence of a five-membered ring fixed on a benzene ring and comprising a ketone function in 1 position, no substitute in 2 or α position and one methyl radical in 3 or β position and the invention protects families of substituted derivatives of the hydrindacen-1-ones and hydro benz(f) inden-1-ones comprising this characteristic group.

Moreover, tests carried out have shown that only the derivatives comprising at least three alkyl (methyl, ethyl or propyl) substitutes on the outer ring which does not carry the ketone function, i.e. on one of the 5,6,6,7,7 positions in the case of a five-membered ring or on one of the 5,5,6,7,8,8 positions in the case of a six-membered ring, presented a musk-like odor usable in perfumes.

Finally, the invention protects, by way of new substances, a family of polycyclic products comprising a central benzene ring, a second lateral ring carrying a ketone function in 1 position, no substitute in 2 position, one methyl group in 3 position and a third lateral ring, five- or six-membered, comprising at least three alkyl substitutes.

Due to their characteristic musk-like odor, these new synthetic products may be used as perfumes or as components of a perfume composition.

The term perfume composition denotes a mixture of one or more products releasing a perfume which may be mixed with various auxiliary substances adapted to fix or stabilize the perfume. Moreover, the mixture may be dissolved in an appropriate solvent or mixed with a fatty or pulverulent substrate and/or with all types of products adapted to facilitate application of the perfume to the skin, hair, etc. . . .

The auxiliary products contained in perfume compositions are well known to the man skilled in the art.

By way of non-limiting example, soaps, detergents, cosmetics such as creams, pomades, toilet waters, before- or after-shave lotions, capillary products, deodorants, etc. . . may be mentioned.

The products according to the invention may be mixed with other perfumes which may be natural products or synthetic perfumes.

The perfume compositions containing compounds according to the invention may be dissolved in solvents, for example in ethanol, monoethyl ether of diethylene glycol, myristate of isopropyl or the esters of β-phenylethyl alcohol, this list not being limitative. The quantity of synthetic musk according to the invention contained in a perfume or in a perfume composition varies considerably depending on the product in which the perfume is incorporated, the nature and quantity of the other constituents of the composition and depending on the intensity of the odor which it is desired to obtain.

A very low proportion by weight, of the order of 0.01%, suffices to give a perfume composition a perceptible musk-like odor.

Examples of composition of perfumes containing artificial musks according to the invention will be given hereinafter, without limitative character.

EXAMPLE 7

| Proportion by weight | Product |
|---|---|
| 90 | Essence of ylang-ylang |
| 150 | phenylethyl alcohol |
| 80 | geraniol |
| 80 | citronellol |
| 30 | heliotropin |
| 50 | linalol |
| 100 | α-methylione |
| 100 | hexyl salicylate |
| 50 | linalyl acetate |
| 20 | 10% undecalactone in diproplylene glycol (DPG) |
| 60 | 10% essence of Moroccan camomile in DPG |
| 35 | Benzyl acetate |
| 5 | dimethylbenzylcarbinol acetate |
| 150 | 3,5,5,6,7 hexamethyl 3,5,6,7-tetrahydro(s) indacen(2H)—1-one |
| TOTAL: 1000 | |

EXAMPLE 8

| Proportion by weight | Product |
|---|---|
| 20 | isobornyl acetate |
| 100 | α-hexylcinnamic aldehyde |
| 50 | linalol |
| 100 | methylionone |
| 50 | ethyl salicylate |
| 70 | terpineol |
| 100 | phenylethyl alcohol |
| 20 | benzyl acetate |
| 30 | essence of lavandin Abrialis |
| 10 | patchouli oil |
| 50 | geraniol |
| 50 | citronellol |
| 50 | cedrenyl acetate |
| 50 | isoeugenyl acetate |
| 50 | piperonyl acetate |
| 200 | 3,5,5,6,7,7-hexamethyl 3,5,6,7-tetrahydro(s) indacen(2H)-1-one |
| Total: 1000 | |

EXAMPLE 9

| Proportions by weight | Product |
|---|---|
| 20 | heliotropin |
| 90 | phenylethyl alcohol |
| 50 | citronellol |
| 30 | benzyl acetate |
| 5 | citral |
| 40 | geraniol |
| 90 | α-hexylcinnamic aldehyde |
| 75 | benzyl salicylate |
| 5 | α-ionone |
| 500 | hydroxycitronellal |
| 20 | phenylpropyl alcohol |
| 10 | 1% 4-(4-hydroxy phenyl) 2-butanone in dipropylene glycol (DPG) |
| 10 | 10% hawthorn in DPG |
| 10 | 10% phenylacetic aldehyde in DPG |
| 10 | 1 °/oo nonadien-2,6-al in DPG |
| 10 | essence of ylang-ylang |
| 25 | 3,5,5,6,7,7-hexamethyl 3,5,6,7-tetrahydro(s) indacen(2H)—1-one |
| TOTAL: 1000 | |

EXAMPLE 10

| Proportions by weight | Product |
|---|---|
| 20 | Patchouli oil |
| 10 | Essence of lavender |
| 80 | geraniol |
| 80 | terpenyl acetate |
| 100 | α-tremineol |
| 50 | tree moss absolute |
| 20 | coumarine |
| 10 | dihydromyrcenol |
| 40 | 1-acetyl 7,10-ethanol 4,4,7-trimethyl-1(9)-octaline |
| 340 | phenylethyl alcohol |
| 100 | linalol |
| 100 | bergamot oil without furocoumarines |
| 50 | 3,5,6,7,7-hexamethyl 3,5,6,7-tetrahydro(s) indacen(2H)—1-one |
| TOTAL: 1000 | |

EXAMPLE 11

| Proportions by weight | Product |
|---|---|
| 10 | attar of roses |
| 40 | essence of ylang-ylang |
| 100 | patchouli oil |
| 150 | essence of geranium Bourbon |
| 250 | essence of lavandin Abrialis |
| 100 | oak moss absolute |
| 50 | 100% eugenol |
| 50 | benzyl salicylate |
| 50 | amyl salicylate |
| 50 | coumarine |
| 30 | α-methyl-p-tert-butylhydrocinnamaldehyde |
| 50 | 4-(4-hydroxy 4-methyl pentyl) cyclohex-3-ene carboxadehyde |
| 20 | phenylethyl alcohol |
| 50 | 3,5,6,7,7-hexamethyl 3,5,6,7-tetrahydro(s) indacen(2H)—1-one |
| TOTAL: 1000 | |

The foregoing Examples refer to perfume compositions all containing 3,5,5,6,7,7-hexamethyl 1,2,3,5,6,7-hexahydro(s) indacen (2H)-1-one, since, among the synthetic derivatives, it is the one having the most pronounced musk-like odor. However, this derivative may be replaced by the other synthetic musks forming the subject matter of the invention and coming under the definition given by the general formula.

The proportion of derivative will vary depending on the olfactive properties of the derivative used.

What is claimed is:

1. New polyalkyl substituted derivatives of indan-1-ones defined by the structural formula:

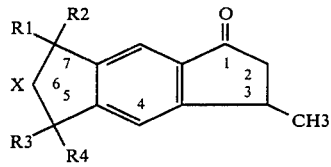

in which R1, R2, R3, R4 denote, separately, a hydrogen or an alkyl radical having one to three atoms of carbon, in which X represents a —CHR5 group or a —CHR5—CHR6— group, in which R5, R6 represent, separately, a hydrogen or a methyl radical and in which at least three of the radicals R1, R2, R3, R4, R5 and R6 are alkyl radicals, which derivatives all comprise a ketone function in 1 position, no substitute in 2 position, one methyl group in 3 position and a five-membered or six-membered ring, symmetrical with respect to the ring bearing the ketone function, comprising at least three alkyl substitutes.

2. A perfume or perfume composition comprising at least one synthetic substance selected from the products defined in claim 1.

3. New products according to claim 1, polyalkyl derivatives of hydro(s) indacen(2H)-1-one, defined by structural formula:

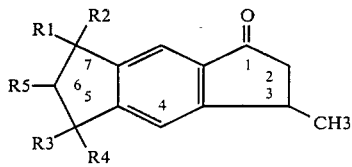

in which R1, R2, R3, R4 represent a hydrogen or an alkyl radical having one to three atoms of carbon, R5 represents a hydrogen or a methyl radical and at least three of the radicals R1, R2, R3, R4, R5 are alkyl radicals.

4. New products according to claim 1, polyalkyl derivatives of hydro-benz(f) inden(1H)-1-one, defined by structural formula:

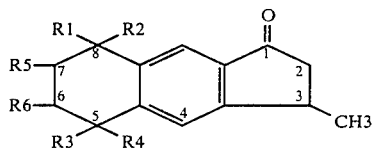

in which R1, R2, R3, R4 represent a hydrogen or an alkyl radical having one to three carbon atoms, R5, R6 represent a hydrogen or a methyl radical and at least three of the radicals R1, R2, R3, R4, R5, R6 are alkyl radicals.

5. A new product according to claim 3, substituted derivative of hydro(s) indacen(2H)-1-one, corresponding to the nomenclature 3,5,5,6,7,7-hexamethyl 3,5,6,7-tetrahydro(s)-indacen(2H)-1-one, having a boiling point of 140°–142° C. under 0.1 mmHg, a refraction index of $n_{20}{}^D = 1.551$ and represented by structural formula:

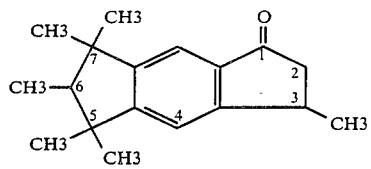

6. A new product according to claim 3, substituted derivative of hydro(s) indacen(2H)-1-one, corresponding to the nomenclature 3,5,5,7,7-pentamethyl 3,5,6,7-tetrahydro(s) indacen(2H)-1-one, having a boiling point of 136°–138° C. under 0.1 mmHg and a melting point of 83°–84° C. and represented by structural formula:

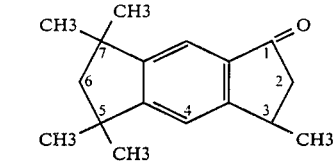

7. New product according to claim 4, substituted derivative of hydro benz(f) inden(1H)-1-one, corresponding to the nomenclature 3,5,5,8,8-pentamethyl 2,3,5,6,7,8-hexahydro benz(f) inden(1H)-1-one, having a boiling point of 143°–144° C. under 0.1 mmHg and a melting point at 80° C. and represented by structural formula:

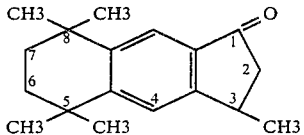

8. A perfume or perfume composition, comprising at least one synthetic substance selected from the group composed of:

3,5,5,6,7,7-hexamethyl 3,5,6,7-tetrahydro(s) indacen(2H)-1-one;

3,5,5,7,7-pentamethyl 3,5,6,7-tetrahydro(s) indacen(2H)-1-one, and 3,5,5,8,8-pentamethyl 2,3,5,6,7,8-hexahydro benz(f) inden(1H)-1-one.

9. A process for synthesizing polyalkyl substituted derivatives of indan-1-ones comprising one methyl radical in 3 position, comprising the following steps of: subjecting an aromatic derivative selected from the group of polyalkyl indanic or tetralinic hydrocarbons to a reaction of cycli-alkylacylation by an α,β-ethylene acid or by a methyl or ethyl ester of an α,β-ethylene acid in the presence of polyphosphoric acid at a temperature of between 90° C. and 150° C., for a duration of between 30 minutes and 180 minutes.

10. A process according to claim 9 for synthesizing 3,5,5,6,7,7-hexamethyl 3,5,6,7-tetrahydro(s) indacen(2H)-1-one, wherein 1,1,2,3,3-pentamethyl indane is reacted with crotonic acid or a methyl or ethyl ester of crotonic acid in polyphosphoric acid.

11. A process according to claim 9 for synthesizing 3,5,5,7,7-pentamethyl 3,5,6,7-tetrahydro(s) indacen(2H)-1-one, wherein 1,1,3,3-tetramethyl indane is reacted with crotonic acid or a methyl or ethyl ester of crotonic acid in polyphosphoric acid.

12. A process according to claim 9 for synthesizing 3,5,5,8,8-pentamethyl 2,3,5,6,7,8-hexahydro(1H)benz(-f)inden(1H)-1-one, wherein 1,1,4,4-tetramethyl tetraline is reacted with crotonic acid or with a methyl or ethyl ester of crotonic acid in the presence of polyphosphoric acid.

13. The process according to claim 9 wherein the temperature is kept between 120° C. and 135° C.

14. The process according to claim 9 which is carried out for a period of 45–70 minutes.

* * * * *